United States Patent
Berndtsson

(10) Patent No.: US 7,521,256 B2
(45) Date of Patent: Apr. 21, 2009

(54) METHOD AND A DEVICE FOR DEFINING A SMALL VOLUME OF A LIQUID SAMPLE

(75) Inventor: Ingemar Berndtsson, Sollentuna (SE)

(73) Assignee: Boule Medical AB, Stockholm (SE)

( * ) Notice: Subject to any disclaimer, the term of this patent is extended or adjusted under 35 U.S.C. 154(b) by 529 days.

(21) Appl. No.: 10/553,866

(22) PCT Filed: Nov. 24, 2004

(86) PCT No.: PCT/SE2004/001729

§ 371 (c)(1),
(2), (4) Date: Oct. 21, 2005

(87) PCT Pub. No.: WO2005/052553

PCT Pub. Date: Jun. 9, 2005

(65) Prior Publication Data

US 2006/0194335 A1   Aug. 31, 2006

(30) Foreign Application Priority Data

Nov. 26, 2003  (SE) .................................... 0303157

(51) Int. Cl.
*G01N 1/18* (2006.01)
(52) U.S. Cl. ........................ 436/177; 422/100; 422/103; 422/93; 436/180; 436/53; 222/335; 222/399
(58) Field of Classification Search ................. 436/180, 436/177; 422/100–103
See application file for complete search history.

(56) References Cited

U.S. PATENT DOCUMENTS

| 4,726,237 | A | 2/1988 | Yung |
| 4,726,932 | A | 2/1988 | Feier et al. |
| 4,896,546 | A | 1/1990 | Cabrera et al. |
| 6,240,984 | B1 * | 6/2001 | Fawcett et al. ............... 141/130 |
| 6,872,361 | B2 | 3/2005 | Li et al. |
| 2002/0172617 | A1 | 11/2002 | Biwa et al. |
| 2003/0099577 | A1 * | 5/2003 | Renaud et al. ............... 422/100 |
| 2005/0118061 | A1 | 6/2005 | Mototsu |

FOREIGN PATENT DOCUMENTS

| JP | 7-137702 A | 5/1995 |
| WO | WO-98/22797 A1 | 5/1998 |
| WO | WO-99/01742 A1 | 1/1999 |
| WO | WO-03/044488 A1 | 5/2003 |

* cited by examiner

*Primary Examiner*—Yelena G Gakh
*Assistant Examiner*—Robert Xu
(74) *Attorney, Agent, or Firm*—Birch, Stewart, Kolasch & Birch, LLP

(57) ABSTRACT

A method and a device for separating a small defined volume of a liquid sample from a relatively large undefined volume of the sample. In a surface of a first body (10) at least one cavity (12) having said small defined volume is provided. The relatively large volume of sample is applied onto the surface and into the cavity. A scraping edge (15) is moved relative to the surface and the cavity, thereby scraping a volume of the relatively large volume from the surface and leaving said small defined volume in the cavity.

15 Claims, 5 Drawing Sheets

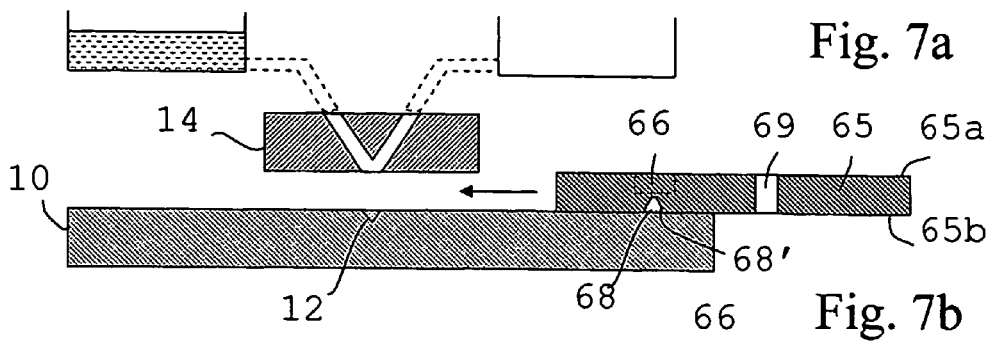
Fig. 7a
Fig. 7b
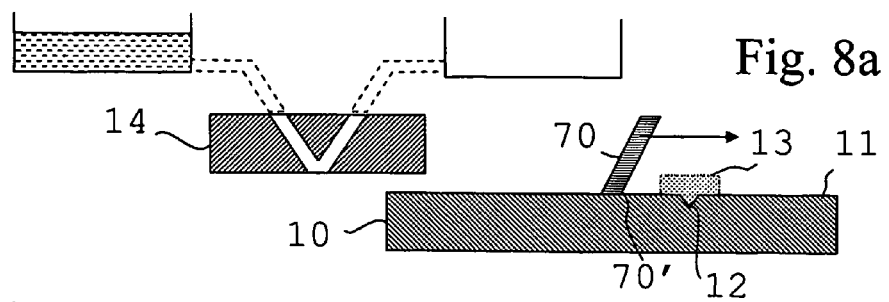
Fig. 8a
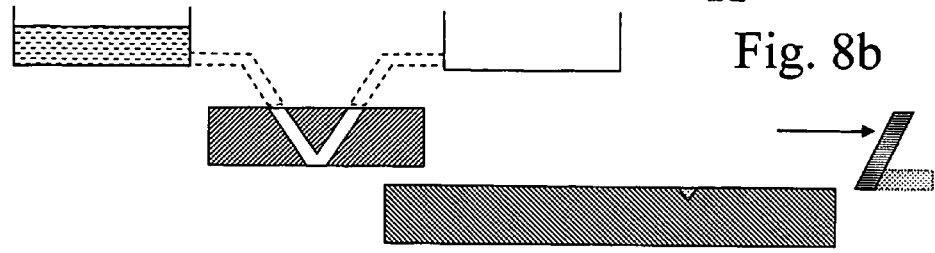
Fig. 8b
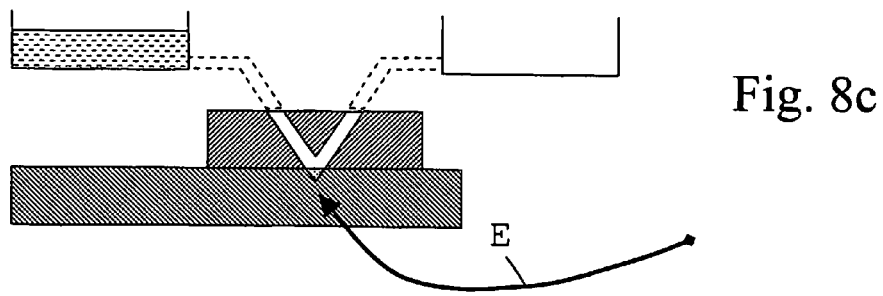
Fig. 8c

METHOD AND A DEVICE FOR DEFINING A SMALL VOLUME OF A LIQUID SAMPLE

The present invention concerns a method and a device for defining a small volume of a liquid sample by separating it from a relatively large undefined volume of said sample, and being useful, for instance, in blood testing, for providing an accurately defined volume of a blood sample.

In blood testing, it is of crucial importance to define an accurate volume of a blood sample, since such accurately defined volume is later on used for certain tests. The accurately defined volume of blood sample is normally diluted by an accurately defined volume of a diluent or a lysing agent, in order to obtain a dilution of typically 1:400 when white blood cells are concerned and typically 1:40000 when counting of red blood cells (RBC) is concerned, in the latter case the dilution normally taking place in two steps. It is obvious, that measurement of sample volumes and dilution liquid volumes must be performed in an accurate and repeatable way such that not only a correct degree of dilution can always be guaranteed but also a thorough and uniform mixing of the two volumes is ensured. Apparently, accurate measurement of sample volumes is the most critical step in the dilution procedure, since the volumes concerned are extremely small compared to the corresponding diluent volumes. A typical sample volume in state of art blood testing devices is 20 µl.

State of art devices frequently utilize turning valves for defining a sample volume to be diluted. Examples of such devices are disclosed in WO 98/22797, WO 99/01742 and WO 03/44488. A turning valve comprises a cylindrical valve body rotatably received within a corresponding cylindrical aperture of a valve housing. A measuring channel having a defined volume extends between opposed positions at the periphery of the valve body. By rotating the valve body between defined positions, the opposed ends of the measuring channel are put into communication with mouths of various channels in the cylindrical aperture of the valve body. Hereby, in one rotational position of the valve housing, the measuring channel may be filled with the defined volume of a sample flowing between two opposed first channel mouths at the inner periphery of the cylindrical aperture. Upon rotation to another rotational position, thereby separating the defined volume from the two opposed first channel mouths and simultaneously putting the opposed ends of the measuring channel in communication with two opposed second channels mouths at the inner periphery of the cylindrical aperture, flushing of the measuring channel with a diluting liquid in order to achieve a desired dilution ratio is enabled.

Although well-functioning, due to their relative complexity, rotating valves are not suited for the mass production desirable for economical production of disposable blood testing equipment.

The present invention aims at providing a simple and reliable method for separating at least one small defined volume of a liquid sample from a relatively large undefined volume of said sample as well as an equally simple, reliable and cheap device for carrying out the method, particularly suited for reproducible mass production.

The method according to the present invention involves the steps of providing in a surface of a first body at least one cavity having said small defined volume; applying said relatively large volume of said sample onto said surface and into said at least one cavity; relatively moving said first body and a scraper means so that said scraper means passes said at least one cavity, thereby scraping a volume of said relatively large volume therefrom and leaving said small defined volume in said at least one cavity.

The device according to the present invention for performing the method includes a first body and a second body. In a surface thereof the first body has at least one cavity (depression, notch, indent, cavity, etching, blasting) having said defined volume. The second body includes an edge relatively slidable along said surface and over the cavity, thereby separating (scraping) an excessive volume of sample from said surface, leaving the defined volume within the cavity.

Embodiments of the present inventions will be described hereinafter, reference being made to the accompanying drawings, wherein:

FIGS. 1a and b are schematic sectional views showing the principle of a device according to the invention shown in a first and a second position, respectively;

Figure 1A:
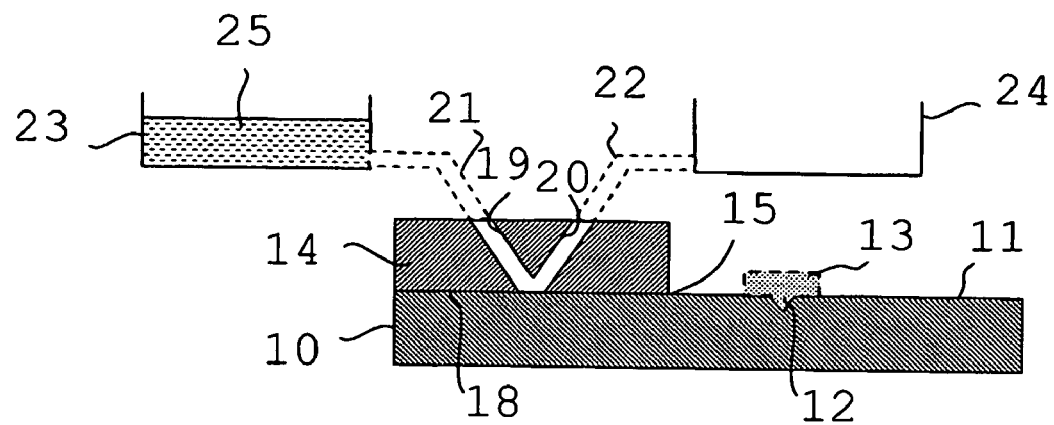
Figure 5A:
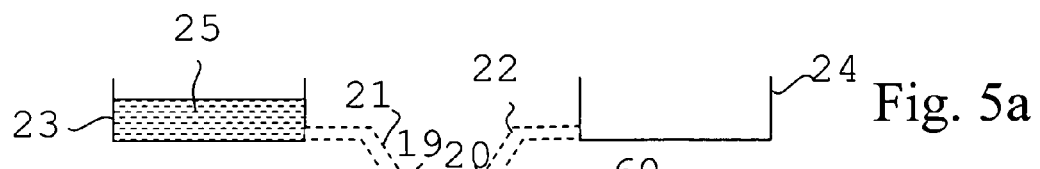
Figure 5B:
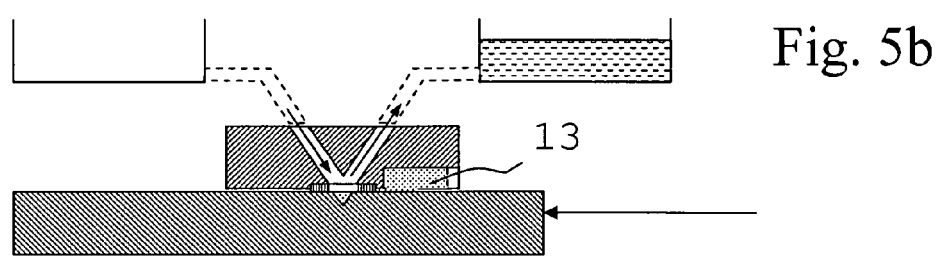
Figure 5C:
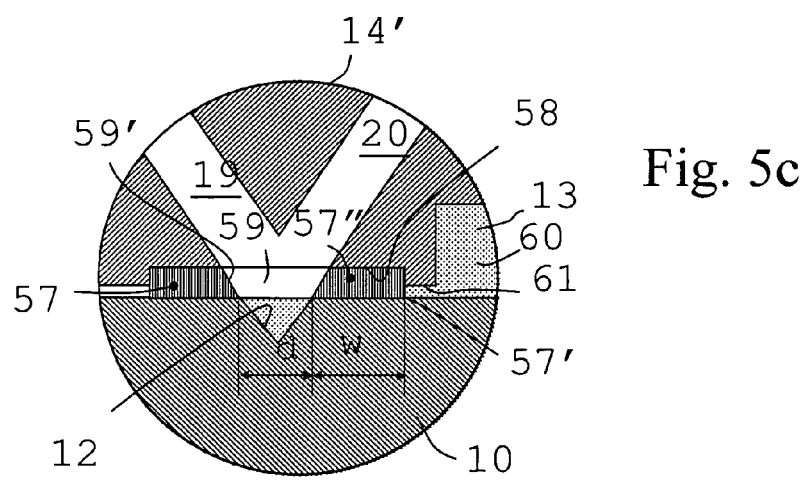
Figure 6:
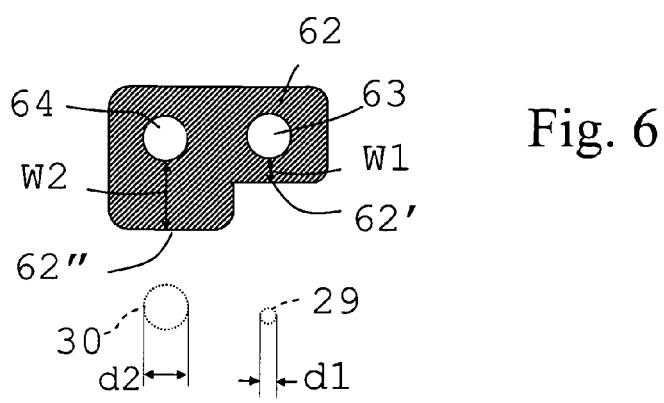
Figure 9A:
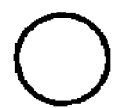
Figure 9B:
Figure 9C:
Figure 9D:
Figure 9E:

FIGS. 5a and b are views similar to those according to FIGS. 1a and b, but showing also a sealing element between the two bodies;

FIG. 5c is an enlargement of a portion of FIG. 5b;

FIG. 6 is a plan view showing an embodiment of a sealing element;

FIG. 7a is a view similar to FIG. 1, but showing an alternative embodiment of the device having a separate body for receiving a sample;

FIG. 7b is a plan view of the separate body of FIG. 7a;

FIGS. 8a, b and c are views similar to FIGS. 1a and b, but showing three consecutive steps in the operation of a device having a separate scraper; and FIG. 9a-e show various examples of cavity configurations and patterns.

The principle of a device embodying the present invention is shown particularly in FIGS. 1a and b.

A first body 10 has a surface 11 in which is provided a cavity 12 having an accurately defined, small volume. An undefined, relatively large volume 13 of a sample, such as a blood sample, is applied onto the surface 11 such that it is ensured that the cavity is filled with sample.

Figure 1B:
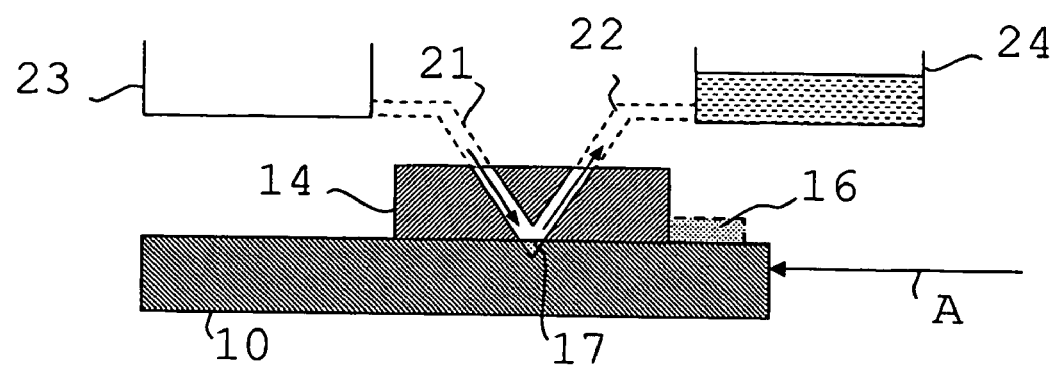

A second body 14 has an edge 15 abutting the surface 11 of the first body. The bodies 10 and 14 are relatively slidable along the surface 11 as indicated by an arrow A, so that the edge, upon passing the cavity, scrapes or shears off a volume 16 of the sample along the surface 11 leaving just the accurately defined, small sample volume 17 within the cavity 12. This situation is shown in FIG. 1b.

In practice, the second body 14 has a surface 18 starting at the edge 15 and facing and abutting the surface 11 of the first body in a fluid tight manner. For the purpose of diluting the accurately defined, small sample volume 17, two channels 19, 20 extend through the second body and open in its surface 18 at positions enabling respective fluid communication with the cavity 12 as shown in FIG. 1b. The channels are shown here to extend in a V-shaped, converging manner towards the surface 18. Evidently, the channels may extend in other directions towards the surface 11 and the cavity 12 therein, including mutually parallel channel directions.

Conduits 21, 22, indicated by broken lines, connect a respective one of the channels 19, 20 with a respective one of receptacles 23, 24. The receptacle 23 is shown in FIG. 1a to contain a defined volume of a liquid 25, such as a diluent or a lysing agent. When the first and second bodies are in the relative position shown in FIG. 1b, flow from the receptacle 23 through the conduit 21 will be directed into the cavity 12, thereby flushing its volume 17 of sample and bringing it through the conduit 22 into the receptacle 24 to provide therein a volume of diluted sample having a defined dilution ratio. The volume of diluted sample may be brought to flow several times forth and back between the two receptacles to ensure proper mixing and dilution, but tests have shown that already one flushing provides a satisfactory result.

Depending on the kind of test to be performed and the dilution ratio desired, the cavity may typically have a volume of between 0,05 and 10 μl, even if it is quite possible to provide cavity volumes of, e.g., between 0,02 and 20 μl.

In practice, it may be useful to provide more than one cavity in the surface of the body 10, for instance one relatively small cavity (e.g. 0,05 μl) and one relatively large cavity (e.g. 10 μl), thereby enabling simultaneous dilution into two different dilution ratios. This is the preferred embodiment of the invention as regards blood analysis.

Figure 2:
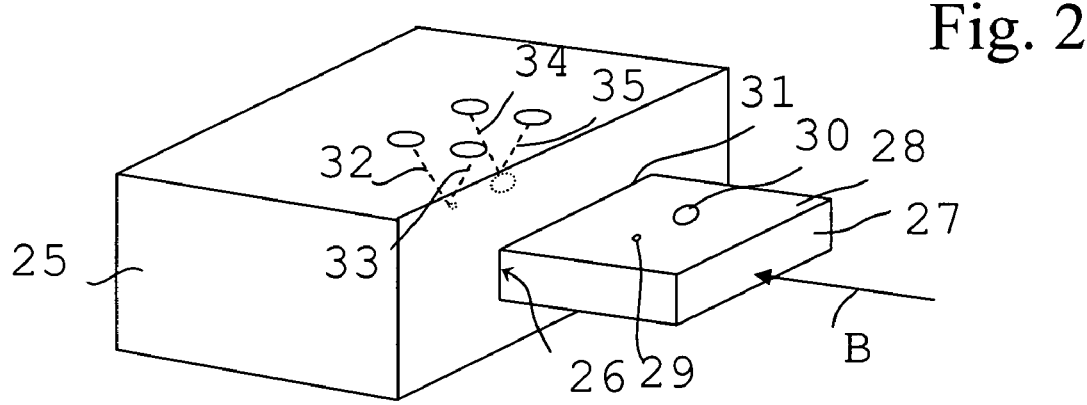
FIG. 2 is a perspective view schematically showing a first principal embodiment of the device.
Figure 3:
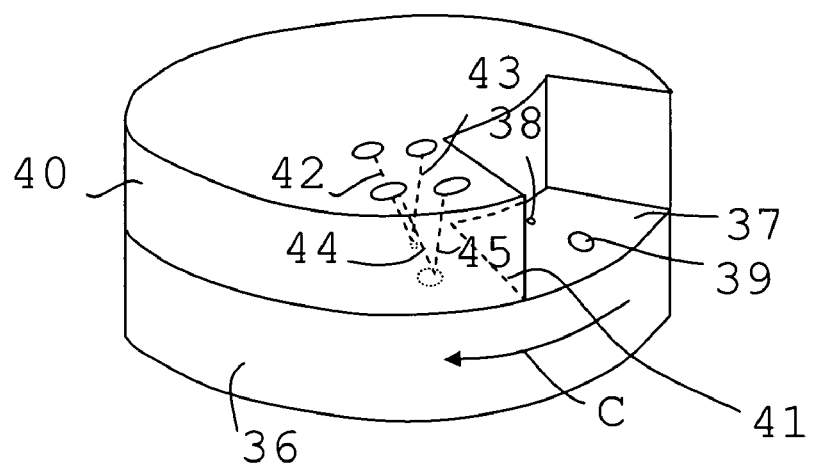
FIG. 3 is a similar view showing a second principal embodiment of the device.
Figure 4:
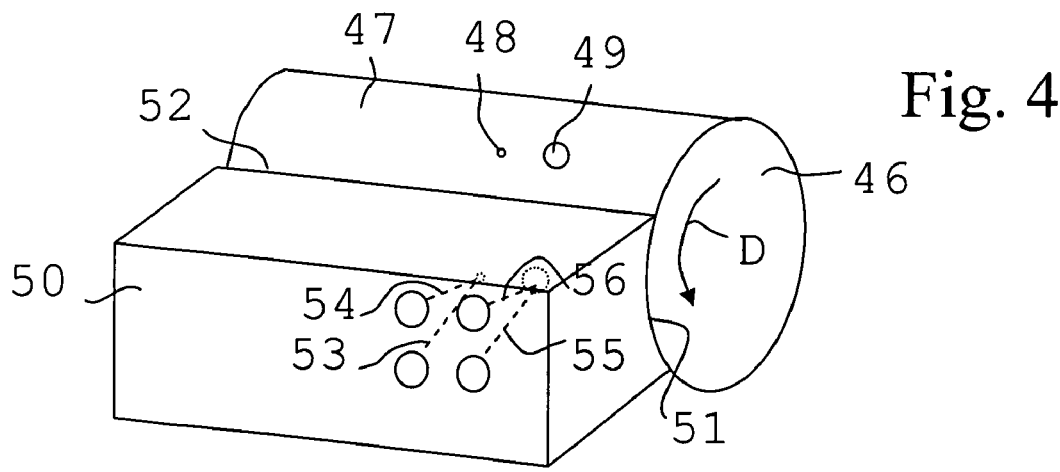
FIG. 4 is a similar view showing a third principal embodiment of the device.

Examples of devices embodying this possibility are shown in FIGS. 2-4.

The embodiment of FIG. 2 comprises a block-shaped housing 25 (second body) having therein a slot 26. A slide 27 (first body) has in an upper surface 28 a smaller cavity 29 and a larger cavity 30. The slot has an edge 31 closely abutting the surface 28. Two pairs of converging channels 32, 33 and 34, 35 extend through the housing 25 and open in a surface of the slot 26 at respective locations corresponding to the positions of the cavities 29, 30. Thus, a non-shown, undefined volume of a sample applied onto the surface 28 will be sheared off by the edge 31 upon sliding the slide 27 into the slot as indicated by an arrow B, leaving two accurately defined volumes of sample in the cavities 29 and 30 to be diluted as explained in connection with FIGS. 1a and b.

In FIG. 3, the first body is a disc-shaped body 36 having in a surface 37 a smaller cavity 38 and a larger cavity 39. The second body is likewise a disc-shaped body 40 having at its circumference a cut-out portion providing access to the surface 37 of the first body and also providing at least one edge 41 abutting the surface 37. Two pairs of converging channels 42, 43 and 44, 45 extend through the body 40 and open in its surface abutting the body 37 at respective locations corresponding to the positions of the cavities 38, 39. Thus, a non-shown, undefined volume of a sample applied onto the surface 37 will be sheared off by the edge 41 upon relatively rotating the two bodies as indicated by an arrow C, leaving two accurately defined volumes of sample in the cavities 38 and 39 to be diluted as explained in connection with FIGS. 1a and 1b.

In FIG. 4, the first body is a cylindrical body 46 having in its peripheral surface 47 a smaller cavity 48 and a larger cavity 49. The second body is a block-shaped body 50 having one surface 51 concavely shaped in conformity with the cylindrical surface 47. An edge 52 of the surface 51 abuts the surface 47. Two pairs of converging channels 53, 54 and 55, 56 extend through the body 50 and open in its surface 51 abutting the body 47 at respective locations corresponding to the positions of the cavities 48, 49. Thus, a non-shown, undefined volume of a sample applied onto the surface 47 will be sheared off by the edge 52 upon relatively rotating the two bodies as indicated by an arrow D, leaving two accurately defined volumes of sample in the cavities 48 and 49 to be diluted as explained in connection with FIGS. 1a and b.

In order to obtain adequate sealing, it is convenient to provide a sealing element 57 between the two bodies 10 and 14 as shown in FIGS. 5a and b and more closely in FIG. 5c.

In this embodiment, an edge 57' of the sealing element takes the place of the edge 15 of the second body 14 in the principal embodiment of FIGS. 1a and b, thus separating the sample volume within the cavity 12 from the remainder of the sample. The sealing element is received within a correspondingly shaped recess 58 in the body 14', thus providing a seal around the cavity and the mouths of the conduits 19, 20.

The sealing element has a through hole or aperture 59 providing communication between the two channels 19, 20 and the cavity 12 in the relative sliding position of the bodies 14' and 10 shown in FIGS. 5b and c.

The second body 14' has a cut-out portion 60, thus guiding and entrapping the larger sample volume 13 upon relative movement between the two bodies (FIG. 5b). The cut-out portion terminates in a relatively narrow slit 61 (FIG. 5c) just before the active edge 57' of the sealing element 57.

As further seen in FIG. 5c, the portion 57" of the sealing element 57 located between the aperture 59 and the edge 57' has a width w exceeding the width d of the cavity 12. Hereby, it is ensured that the mouth of the cavity is completely sealed as the portion 57" of the sealing element passes over it upon relative movement of the two bodies.

As an alternative to the sealing element shown in FIGS. 5a and b having side walls directed perpendicularly to the surface 11 of the first body 10, the aperture 59 is shown in FIG. 5c to have side walls 59' inclined approximately in conformity with the inclination of the channels 19 and 20.

FIG. 6 shows an embodiment of a sealing element 62 useful for sealing of two cavities, for instance the relatively small cavity 29 and the relatively large cavity 30 in the embodiment according to FIG. 2. For the purpose of illustration only, the locations of these cavities are shown in FIG. 2 with dashed lines. The sealing element has two apertures 63 and 64. In order to provide sealing of both apertures during the entire relative movement of the body 27 and the sealing element, the latter is substantially L-shaped, i.e., the apertures are aligned but the active edge of the sealing element is divided into two edge portions 62', 62" such that the respective portions of the sealing element located between the apertures and the edge portions have different widths W1 and W2, respectively, both being greater than the respective cavity width d1, d2, respectively.

I FIG. 7a, a separate body 65 is slidably movably placed between the first body 10 and the second body 14. It has in its surface 65a facing the second body 14 a sample receiving aperture 66 communicating through a channel 67 with a sample holding cavity 68 in its surface 65b facing the first body 10. Thus, at least a portion of a blood sample, for instance, applied into the aperture 66 will be transferred into the cavity 67. A through hole 69 extends through the body 65.

Upon relative movement of the body 65 and the first and second bodies, a portion of the sample volume contained within the sample holding cavity 68 will be entrapped within the cavity 12 in the first body 10, completely filling it. A trailing edge 68' of the cavity 68 will act as a scraping edge ensuring that superfluous amounts of sample is removed from the sample volume to be further treated. The through hole 69 provides for communication between the channels 19, 20 and the cavity 12. It should be noted here, that the relative dimensions between the various items shown and described are for illustrative purposes only.

In the embodiment shown in FIGS. 8a-c, a separate scraper 70 having a scraping edge 70' is provided and is used for scraping off superfluous sample from the surface 11 around the cavity 12. In this embodiment, the two bodies 10 and 14 are initially and during the scraping operation (FIGS. 8a and b) spaced from each other. After the scraping operation is finished, the two bodies are caused to approach one another along an arcuate path as indicated by the arrow E in FIG. 8c so as to bring the bodies in a position to perform the flushing operation.

FIG. 9 shows various cavity shapes and configurations. FIG. 9a shows a part-spherical shape, FIG. 9b shows a pattern of a plurality of substantially circular depressions, FIG. 9c shows a square or pyramidal depression, FIG. 9d shows a number of parallel grooves, and FIG. 9e shows a rectangular cavity shaped by, e.g., etching, blasting, cutting or the like material removing method.

The invention claimed is:

1. A sample volume defining device for separating and diluting a small defined volume of a liquid sample, said device comprising:
   (a) a first body comprising at least one cavity with a defined volume on a surface of said first body, said cavity having an open end and an opposing closed end; said first body being slidable between a first location and a second location; and
   (b) a second body having a surface complementary with and abutting against said surface of said first body in a manner, when said first body being in said first location, an area of said surface of said first body around said cavity not being in contact with said surface of said second body and being available for applying said liquid sample thereon, and a pair of channels extending through said second body, each of said channels having an opening on said surface of said second body; when said first body being in said second location, said pair of channels being in fluid communication with said cavity of said first body;

when said first body is slid from said first location to said second location, an edge of said second body, abutting said surface of said first body, scrapes off an excessive volume of said liquid sample applied over said cavity and on said area, and leaves within said cavity a volume of said liquid sample equal to said defined volume of said cavity; and at said second location, said pair of channels of said second body are in fluid communication with said cavity, enabling directing a flow of a diluting fluid from one of said channels to flush said liquid sample retained in said cavity through another of said channels to form a diluted sample.

2. The device of claim 1 further comprising two receptacles, each connecting with one of said channels, and one of said receptacles containing a defined volume of said diluting fluid.

3. The device of claim 2, wherein said diluted sample has a defined dilution ratio.

4. The device of claim 1, wherein said defined volume of said cavity is from 0.02 to 20 μl.

5. The device of claim 1, wherein said openings of said pair of channels are converged.

6. The device of claim 1, wherein said channels of said second body are in fluid communication.

7. The device of claim 1, wherein said second body further comprises a sealing element disposed in a recess on said surface abutting against said first body; said sealing element having an aperture aligned with said openings of said pair of channels, providing a seal around said openings of said channels.

8. The device of claim 7, wherein a portion of said sealing element between said aperture and an edge facing said cavity when said first body is in said first position has a width exceeding a corresponding width of said cavity.

9. The device of claim 1 further comprising a second cavity with a second defined volume on said surface of said first body, said second cavity having an open end and an opposing closed end; and said second body including a second pair of channels extending through said second body, each thereof having an opening on said surface of said second body; when said first body being in said second location, said second pair of channels being in fluid communication with said second cavity of said first body; said second body abutting against said surface of said first body in a manner, when said first body being in said first location, an area of said surface of said first body around said second cavity not being in contact with said surface of said second body and being available for applying said liquid sample thereon;

wherein when said first body is slid from said first location to said second location, said edge of said second body scrapes off an excessive volume of said liquid sample applied over said second cavity and on said area around said second cavity, and leaves within said second cavity a volume of said liquid sample equal to said second defined volume; and at said second location, said second pair of channels are in fluid communication with said second cavity, enabling directing a flow of said diluting fluid from one of said second pair of channels to flush said liquid sample retained in said second cavity through another of said second pair of channels to form a second diluted sample.

10. The device of claim 9, wherein said first cavity and said second cavity have different volumes.

11. The device of claim 9, wherein said second body further comprises a sealing element disposed in a recess on said surface abutting against said first body; said sealing element having two apertures, each aligned with said openings of each of said pairs of channels, providing seals around said openings of each of said pairs of channels.

12. A method of separating and diluting a small defined volume of a liquid sample comprising:
   (a) providing a device comprising a first body including at least one cavity with a defined volume on a surface of said first body, said cavity having an open end and an opposing closed end; said first body being slidable between a first location and a second location; and a second body having a surface complementary with and abutting against said surface of said first body, and a pair of channels extending through said second body, each of said channels having an opening on said surface of said second body; when said first body being in said second location, said pair of channels being in fluid communication with said cavity of said first body;
   (b) applying a relatively large undefined volume of said liquid sample in said cavity, with an excessive volume over said cavity and onto an area of said surface of said first body around said cavity;
   (c) sliding said first body from said first location to said second location, thereby an edge of said second body, abutting against said surface of said first body, scraping off said excessive volume of said liquid sample over said cavity and leaving within said cavity a volume of said liquid sample equal to said defined volume of said cavity; and
   (d) flushing said defined volume of said liquid sample retained in said cavity by a flow of a diluting fluid from one of said channels out of said cavity and through another of said channels to form a diluted sample.

13. The method of claim 12, wherein said diluting fluid has a defined volume, and said diluted sample has a defined dilution ratio.

14. The method of claim 12, wherein said device further comprising a second cavity with a second defined volume on said surface of said first body, said second cavity having an open end and an opposing closed end; and said second body including a second pair of channels extending through said second body, each thereof having an opening on said surface of said second body; when said first body being in said second location, said second pair of channels being in fluid communication with said second cavity; and wherein said method further comprises:

in (b) applying a second relatively large undefined volume of said liquid sample in said second cavity, with an excessive volume over said second cavity and on an area of said surface of said first body around said second cavity;

in (c) when sliding said first body from said first location to said second location, said edge of said second body scrapes off said excessive volume of said liquid sample over said second cavity, and leaving within said second cavity a volume of said liquid sample equal to said second defined volume of said second cavity; and in (d) flushing said second defined volume of said liquid sample retained in said second cavity by a flow of said diluting fluid from one of said second pair of channels out of said second cavity and through another of said second pair of channels to form a second diluted sample.

15. The method of claim 14, wherein said diluted samples have two different dilution ratios.

* * * * *